United States Patent
Brown et al.

(10) Patent No.: US 6,645,214 B2
(45) Date of Patent: Nov. 11, 2003

(54) APPARATUS AND METHOD FOR BONE POSITIONING

(75) Inventors: Scott C. Brown, Warsaw, IN (US); Hal S. Crane, Denver, CO (US)

(73) Assignee: DePuy Orthopaedics, Inc., Warsaw, IN (US)

(*) Notice: Subject to any disclaimer, the term of this patent is extended or adjusted under 35 U.S.C. 154(b) by 0 days.

(21) Appl. No.: 10/013,810

(22) Filed: Nov. 12, 2001

(65) Prior Publication Data

US 2003/0093080 A1 May 15, 2003

(51) Int. Cl.$^7$ ................................. A61B 17/58
(52) U.S. Cl. ..................... 606/102; 606/86; 606/89
(58) Field of Search ..................... 606/102, 88, 89, 606/86, 96, 99, 100; 128/774, 782; 33/511, 512, 515

(56) References Cited

U.S. PATENT DOCUMENTS

| 4,270,724 A | * | 6/1981 | McMullen ............... 606/102 |
| 5,122,145 A | | 6/1992 | Fishbane |
| 5,616,147 A | | 4/1997 | Gadelius |
| 5,700,268 A | | 12/1997 | Bertin |
| 5,788,705 A | | 8/1998 | Huddleston et al. |
| 5,814,050 A | | 9/1998 | Benson |
| 5,997,545 A | | 12/1999 | Doherty et al. |
| 6,010,509 A | | 1/2000 | Delgado et al. |
| 6,027,507 A | | 2/2000 | Anderson et al. |
| 6,173,200 B1 | | 1/2001 | Cooke et al. |
| 6,193,724 B1 | | 2/2001 | Chan |

FOREIGN PATENT DOCUMENTS

| FR | 2 775 889 | 9/1999 |
| WO | WO 94/12109 | 6/1994 |
| WO | WO 96/40021 | 12/1996 |
| WO | WO 00/32093 | 6/2000 |
| WO | WO 01/30247 | 5/2001 |

* cited by examiner

Primary Examiner—Pedro Philogene
Assistant Examiner—D. Austin Bonderer
(74) Attorney, Agent, or Firm—Maginot, Moore & Beck

(57) ABSTRACT

An apparatus for use in an arrangement for measuring the relative position of two bones during surgery includes a clamp and a measurement arm. The clamp is adapted to engage and secure to an anchor in a fixed vertical position, the anchor being secured to a first bone location. The measurement arm comprises an elongate portion and a locator portion that extends angularly from the elongate portion. The measurement arm is slidably supported on the clamp. The measurement arm is further rotatably supported on the clamp at a position in which an axis of rotation of the measurement arm is spaced apart from a longitudinal axis of the anchor.

28 Claims, 7 Drawing Sheets

APPARATUS AND METHOD FOR BONE POSITIONING

FIELD OF THE INVENTION

The present invention relates generally to surgical methods and apparatus, and in particular, to methods and apparatus for bone positioning during surgery.

BACKGROUND OF THE INVENTION

An important aspect of certain types of surgery, particularly arthroplastic surgery, is proper bone positioning. Bone positioning involves proper selection and implantation of a prosthetic component such that it does not change the natural posture and attitude of the remaining bones.

By way of example, total hip replacement surgery requires appropriate selection of the hip prosthesis to avoid changing the overall length and lateral offset of the leg. Unequal leg length and/or lateral offset can undesirably result in a persistent limp in the patient. However, if a hip prosthesis having the correct dimensions is selected, then appropriate leg length and lateral offset may be accomplished.

A general technique that facilitates the selection of an appropriately-sized prosthetic involves performing a reference measurement prior to the hip replacement, and then adjusting the size of the prosthetic until the reference measurement can be reproduced. Once the size of the prosthetic results in a measurement that is largely identical to the initial reference measurement, then a prosthetic of that size is employed within the patient.

Many methods of performing bone positioning measurements have been developed. Most of these methods employ a reference pin that is implanted into the patient's ilium. Another device is then used to measure the length from the implanted pin to a reference point on the femur. For example, U.S. Pat. No. 6,027,507 to Anderson et al. shows a leg length gauge that employs a pin attached to a patient's ilium and a second pin attached to the patient's femur. The gauge includes two vertical rods that fit on top of the pins, and a horizontal rod that is secured to the two vertical rods. The length between the two vertical rods may be adjusted to accommodate the distance between the two pins by sliding the horizontal rod with respect to one of the vertical rods. Once adjusted to the appropriate length, the two vertical rods should fit on the two pins in the ilium and femur. The vertical rods and horizontal rod are removed as a unit, retaining the appropriate length measurement. After replacement of the hip, the rod assembly is placed over the pins. If the vertical rods do not fit, then an adjustment in the prosthetic fit or length is indicated. If the vertical rods fit over the pins, then the prosthetic size is correct.

Other prior art patents, including U.S. Pat. No. 5,814,050 to Benson and U.S. Pat. No. 5,122,145 to Fishbane use similar devices that rely upon measuring the distance between reference pins in the ilium and the femur. However, the above cited prior art patents suffer from various shortcomings that limit their usefulness in bone positioning during total hip replacement surgery. For example, many of the techniques and devices taught in those patents are difficult to use because, among other things, they require the placement of multiple bone pins. Such devices also present difficulties in aligning the measurement device.

In addition, many prior art devices, including some of the devices identified above, measure only length, and do not adequately measure lateral offset. The failure to provide reliable lateral offset measurements can result in improper final bone positioning after implantation of the prosthesis.

One prior art device shown in U.S. Pat. No. 6,193,724 to Chan (the "Chan device") addresses some of the above needs through the use of an adjustable outrigger device and an anchor pin that is attached to the ilium. The adjustable outrigger extends horizontally from the ilium pin and terminates in a vertically-oriented pointer. The height and length of the outrigger may be adjusted such that the vertical pointer touches a predetermined spot on the femur. In this manner, the lateral offset may be measured (by adjusting the height) and the length may be measured (by adjusting the length). However, one drawback to the Chan device is that if the anchor pin is not perfectly aligned with the axis of the femur, then reproducing the exact alignment of the femur with respect to the ilium can be difficult. Moreover, locking the movable outrigger into position once a measurement has taken place undesirably requires additional tools.

What is needed, therefore, is a device that assists in bone positioning measurements that is relatively easy to use. A further need exists for such a device that is capable of performing both bone length and lateral offset measurements.

SUMMARY OF THE INVENTION

The present invention addresses the above needs as well as others through a device that attaches to an anchor and facilitates accurate and repeatable offset and length measurements.

A first embodiment of the present invention is an apparatus for use in an arrangement for measuring the relative position of two bones during surgery. The apparatus includes a spring-biased clamp and a measurement arm. The spring biased clamp has first and second opposing clamping surfaces that adapted to engage and secure the clamp to an anchor in a fixed vertical position. The anchor is secured to a first bone location. The measurement arm comprises an elongate portion and a locator portion. The locator portion extends angularly from the elongate portion. The measurement arm is slidably supported on the spring biased clamp.

Accordingly, the above-described embodiment employs a spring-biased clamp for fixing the device to an anchor. The use of the spring-biased clamp, among other things, increases convenience of use by eliminating or reducing the need for additional tools to either secure or remove the device.

A second embodiment of the invention is also an apparatus for use in an arrangement for measuring the relative positioning of two bones during surgery. In the second embodiment the apparatus includes a clamp and a measurement arm. The clamp is adapted to engage and secure to an anchor in a fixed vertical position, the anchor being secured to a first bone location. The measurement arm comprises an elongate portion and a locator portion that extends angularly from the elongate portion. The measurement arm is slidably supported on the clamp. The measurement arm is further rotatably supported on the clamp via a spring biased clamping element.

Similar in some respects to the first embodiment, the second embodiment employs a spring biased clamp. However, in this embodiment the spring biased clamping mechanism secures the rotational position of the measurement arm. Such a device allows for rotational movement of the measurement arm, which increases the adaptability of the device, while incorporating the convenience of a spring-biased clamp.

Yet another embodiment of the present invention is an apparatus for use in an arrangement for measuring the relative position of two bones during surgery that also includes a clamp and a measurement arm. The clamp is adapted to engage and secure to an anchor in a fixed vertical position, the anchor being secured to a first bone location. The measurement arm comprises an elongate portion and a locator portion that extends angularly from the elongate portion. The measurement arm is slidably supported on the clamp. The measurement arm is further rotatably supported on the clamp at a position in which an axis of rotation of the measurement arm is spaced apart from a longitudinal axis of the anchor.

The above describe features and embodiments, as well as others, will become more readily apparent to those of ordinary skill in the art by reference to the following detailed description and accompanying drawings.

DETAILED DESCRIPTION

Figure 1:
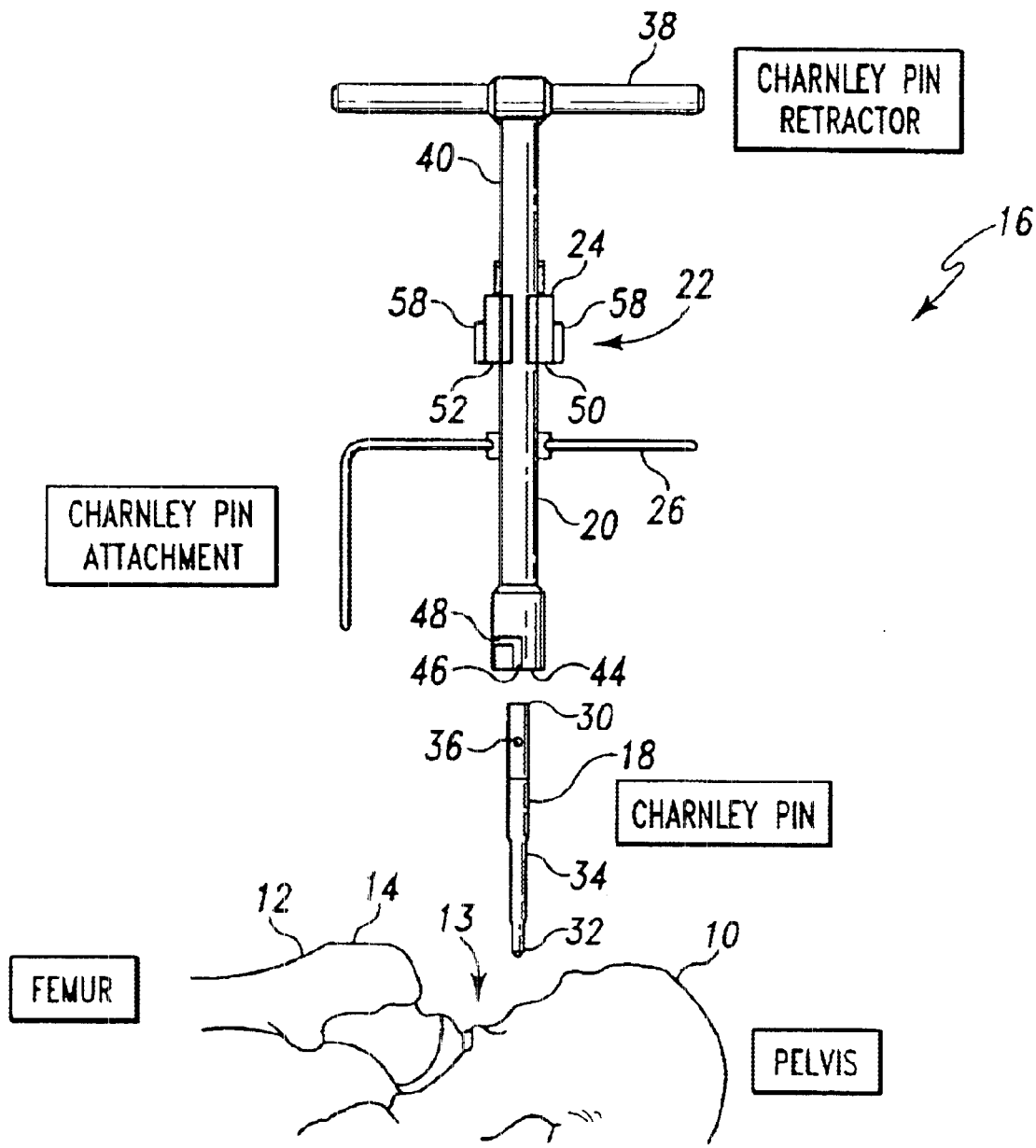
FIG. 1 shows a partially exploded perspective view of an exemplary embodiment of a measuring arrangement according to the present invention in the vicinity of the hip bones.
Figure 2:
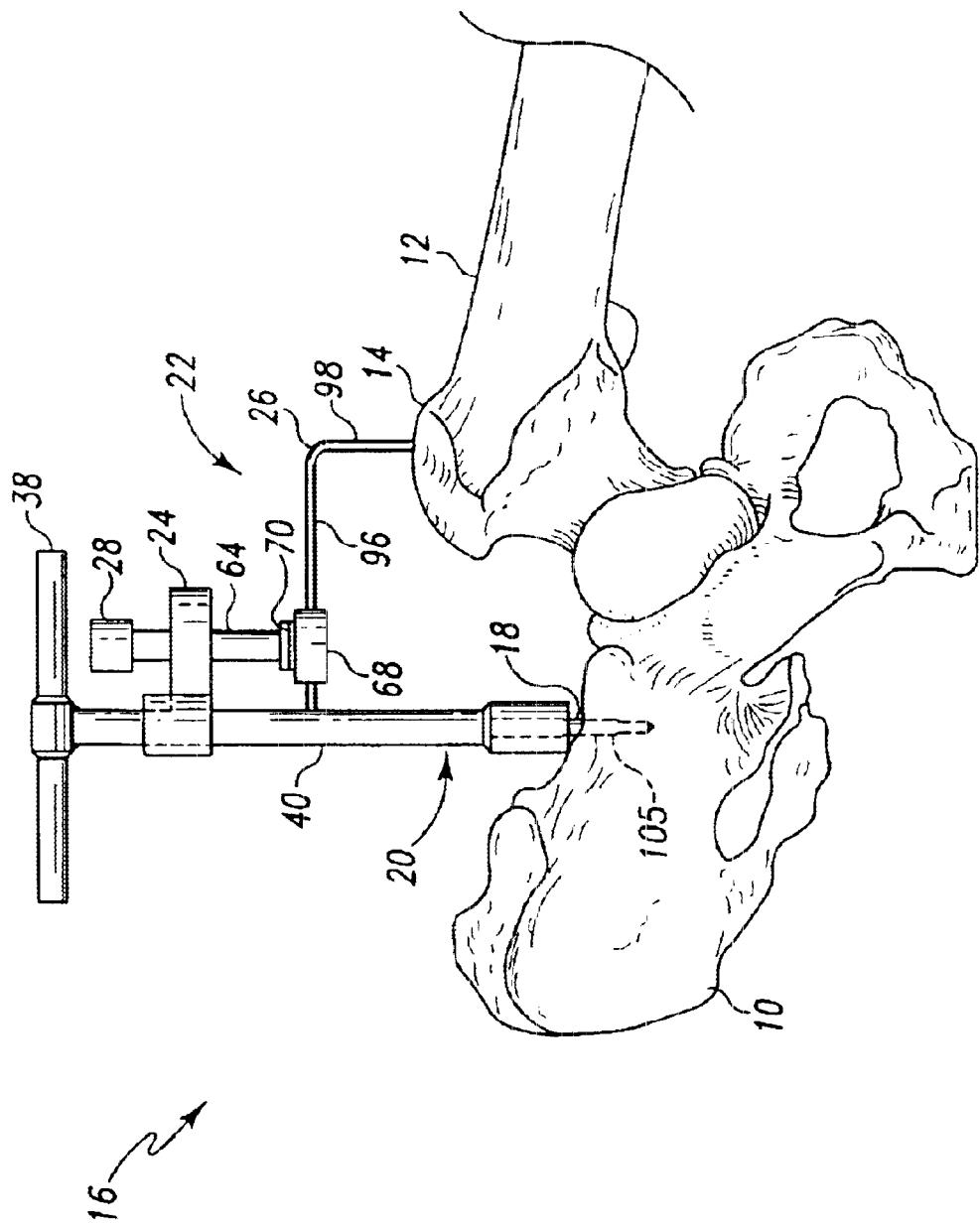
FIG. 2 shows a perspective view of the measuring arrangement of FIG. 1 employed in performing hip bone measurements in accordance with the present invention.

FIG. 1 shows a partially exploded perspective view of an exemplary embodiment of a measuring arrangement 16 according to the present invention in the vicinity of the hip bones. In particular, FIG. 1 shows fragmentary portions of the ilium 10 and the femur 12 in the vicinity of the hip joint 13. In general, a surgeon employs the measuring arrangement 16 to measure the distance and offset between an anchor point on the ilium 10 and a predetermined feature on the femur 12. To this end, an anchor pin 18 is employed to mark and hold a reference point on the ilium 10 and the greater trochanter 14 may be employed as the predetermined feature on the femur 12. FIG. 2 illustrates an exemplary measurement taken between the anchor pin 18 in the ilium 10 and a point on the greater trochanter 14.

In general, the surgeon makes the measurement before and after hip replacement in order to ensure that the hip replacement prosthesis provides the appropriate leg length and offset. In accordance with a method according to the invention, various trial hip prostheses, not shown, may be implanted until one yields length and offset measurements substantially similar to those taken prior to replacement. Alternatively, an adjustable hip prosthesis may be used and adjusted to obtain the appropriate length and offset measurements.

The measuring arrangement 16 includes the anchor pin 18, a pin sleeve 20 and a pin attachment device 22. The pin sleeve 20 is a device that fits over at least a portion of the pin to provide a vertical (i.e. lateral with respect to the body) extension of the reference point identified by the anchor pin 18. The pin sleeve 20 is removable to allow for greater access to the surgical site after the initial measurement has taken place. It will be appreciated, however, that the anchor pin 18 may suitably be made long enough to eliminate the need for the pin sleeve 20 for measurement purposes if the additional access provided by removal of the sleeve 20 is not necessary.

The pin attachment device 22 is a device that attaches to the anchor pin 18, in this case, via the pin sleeve 20. The pin attachment device 22 performs the measurements for both length and offset, as will be discussed below. The pin attachment device 22 has many features that both individually and collectively improve the convenience of the bone measurement operation. By way of example, the pin attachment device 22 includes a measurement arm 26 that is movable both linearly (inferior-superior direction) and rotationally (about a vertical or anterior-posterior axis). In addition, such horizontal and linear movement may be locked in place using spring-loaded clamping mechanisms, which provide various advantages over bolt or screw type locking mechanisms. Furthermore, the pin attachment device 22 includes a second axis of rotation, which allows the measurement arm 26 to be aligned with the axis of the femur even if the anchor pin 18 is offset in the medial-lateral direction from the center of the femur. Several other features will be discussed below. It will be noted that incorporation of some, but not all, of the inventive features discussed herein will provide at least some benefits of convenience and/or accuracy in bone positioning measurement.

Figure 3:
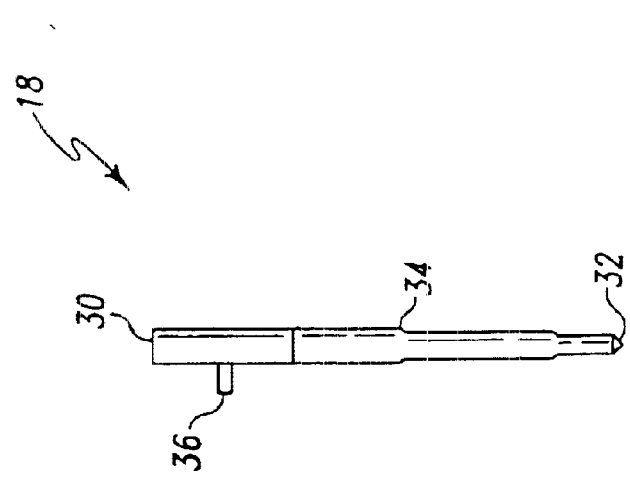
FIG. 3 shows an exemplary anchor pin that may be used in the measuring arrangement of FIG. 1.

Referring to FIGS. 1 and 3, the exemplary anchor pin 18 of the measuring apparatus includes a proximal end 30, a distal end 32, and a pin shaft 34 disposed therebetween. Near the proximal end 30 is a post 36 that provides a mechanical leverage or gripping point for removing the anchor pin 18 from the bone after surgery. The distal 32 end may suitably have a tapered or pointed end to facilitate penetration into the bone. The anchor pin 18 should be constructed of a material having sufficient strength, for example, stainless steel, to withstand hammering force.

Figure 5:
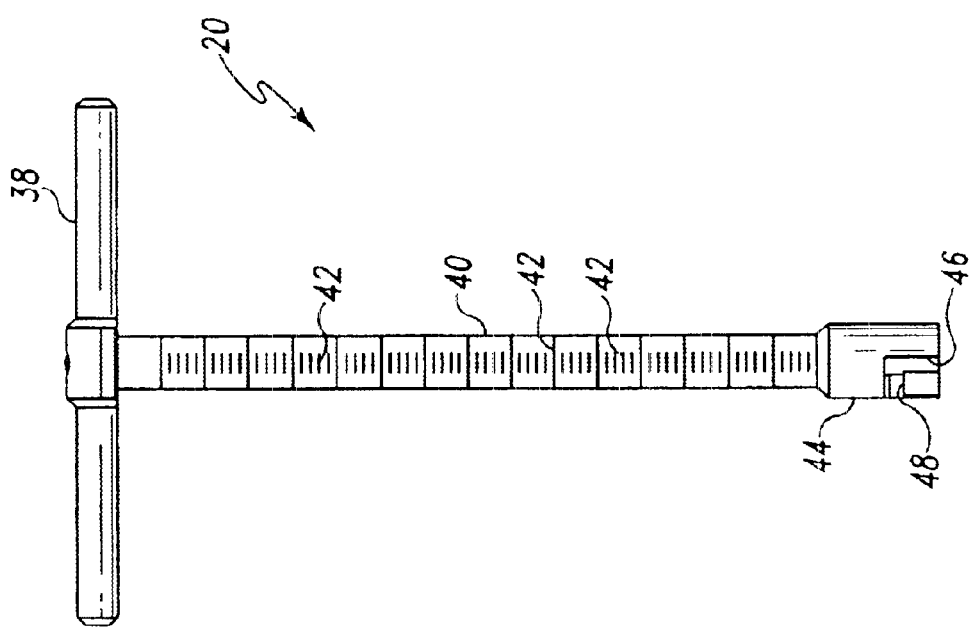
FIG. 5 shows a front plan view of the pin sleeve of FIG. 4.
Figure 4:
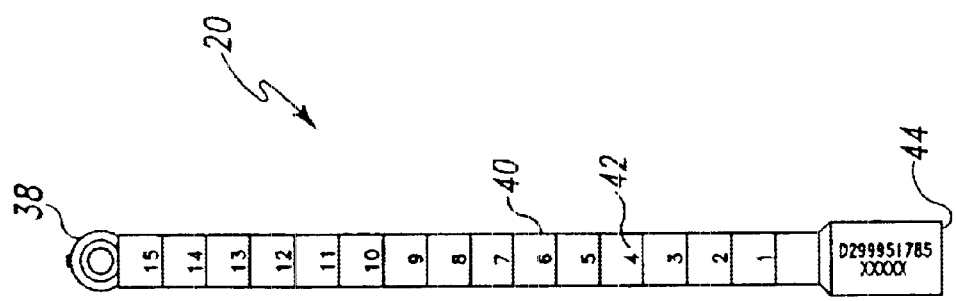
FIG. 4 shows a side plan view of an exemplary pin sleeve that may be used in the measuring arrangement of FIG. 1.

Referring to FIGS. 1, 4 and 5, the exemplary pin sleeve 20 of the present invention includes a handle 38 and a shaft 40. The exemplary handle 38 shown in FIGS. 1, 4 and 5 is basically a bar or rod handle disposed perpendicularly to the shaft 40 at the proximal end of the shaft 40. However, other suitable handle configurations may be used. The shaft 40 includes measurement indicia 42 that provide an index by which the vertical location of the pin attachment device 44 may be measured, as will be discussed below. The measurement indicia 42 may include ruled markings (FIG. 5) and/or numbered markings (FIG. 4).

At the distal end of the shaft 40 is a pin cavity 44. The pin cavity 44 comprises a bore or other opening that receives at least the proximal end 30 of the anchor pin 18. The shaft 40 includes an arrangement in the vicinity of the pin cavity 44 for receiving and engaging the post 36 of the anchoring pin 18 to assist in removing the anchoring pin 18 from the bone. In particular, the shaft 40 includes a post channel 48 that extends around a portion of the periphery of the shaft 40 near the distal end of the shaft 40. The post channel 48 is configured to receive the post 36 when the anchoring pin 18 is partially disposed within the pin cavity 44. In such a position, the material of the shaft 40 below the post channel 48 engages the post 36 when the shaft 40 is pulled upward by the handle 38. Such engagement urges the anchoring pin 18 upward and out of the bone.

To facilitate insertion of the post 36 into the post channel 48, the shaft 40 further includes includes a vertical channel 46 that extends from the distal extreme edge of the shaft 40 to the post channel 48. The vertical channel 46 thus provides an arrangement by which the pin sleeve 20 may be latched onto the anchor pin 18. In particular, to place the pin sleeve 20 onto the anchor pin 18, the surgeon aligns the vertical channel 46 with the post 36, and then places the pin sleeve 20 over the anchoring pin 18 such that the proximal end 30 of the anchoring pin is within the pin cavity 44. Once the anchoring pin 18 is sufficiently within the pin cavity 44, the post 36 enters into the post channel 48 at the intersection between the post channel 48 and the vertical channel 46. The surgeon then twists or torques the pin sleeve 20 so that the post 36 is no longer aligned with the vertical channel 46. Removal of the pin sleeve 20 from the anchor pin 18 is accomplished by reversing the above procedure.

In normal operation, the anchor pin 18 is implanted into bone tissue by disposing the anchor pin 18 within the pin sleeve 20 as discussed above, positioning the distal end 32 at the point of implantation, and then impacting the pin sleeve 20. Thereafter, the surgeon may remove the anchoring pin 18 by pulling on the handle 38 of the pin sleeve 20.

Figure 6:
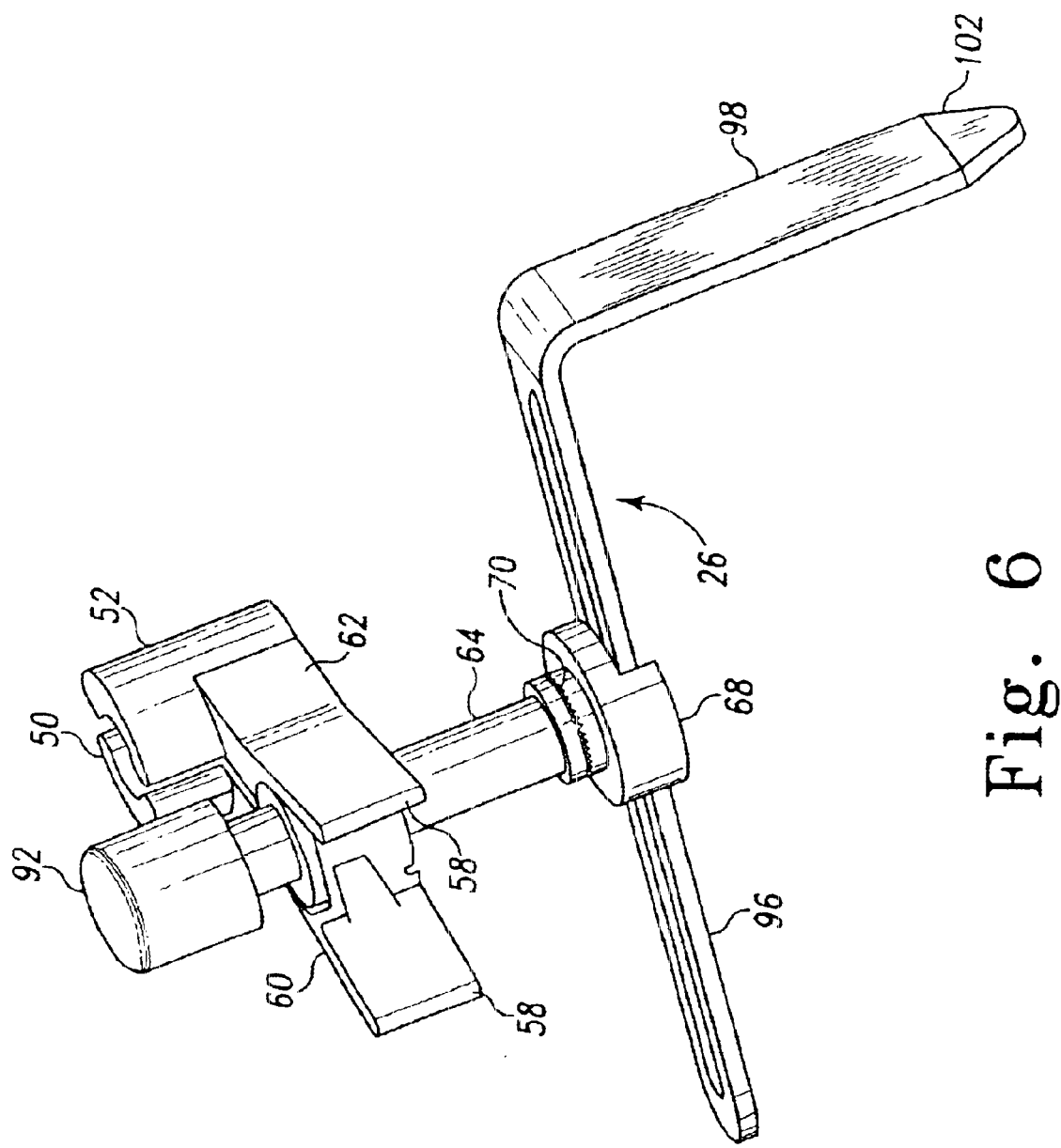
FIG. 6 shows a perspective view of an exemplary embodiment of the measurement attachment apparatus of the measuring arrangement of FIG. 1.
Figure 7:
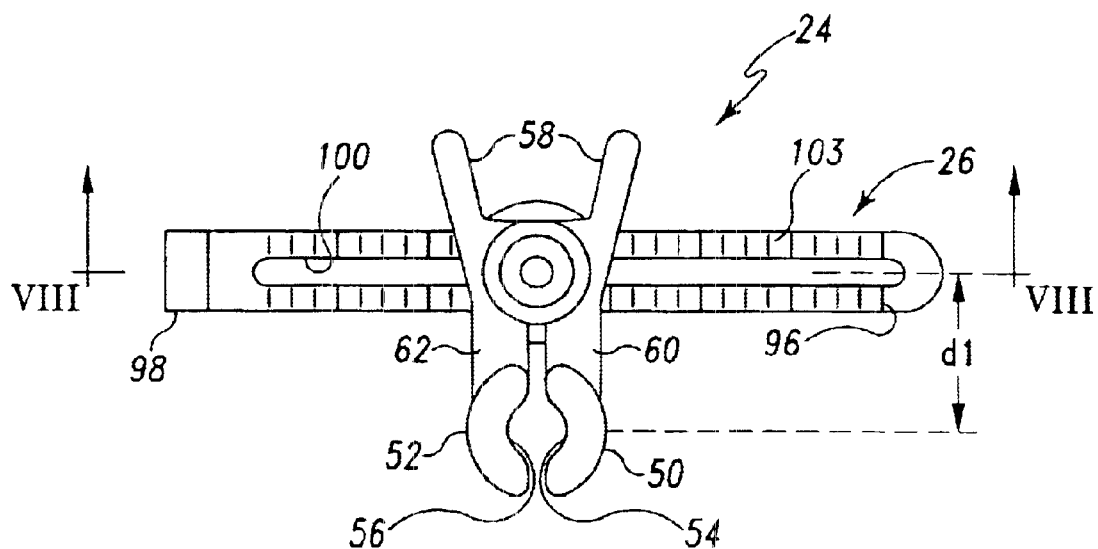
FIG. 7 shows a top plan view of the measurement attachment apparatus of FIG. 6 in a first rotational position.
Figure 8:
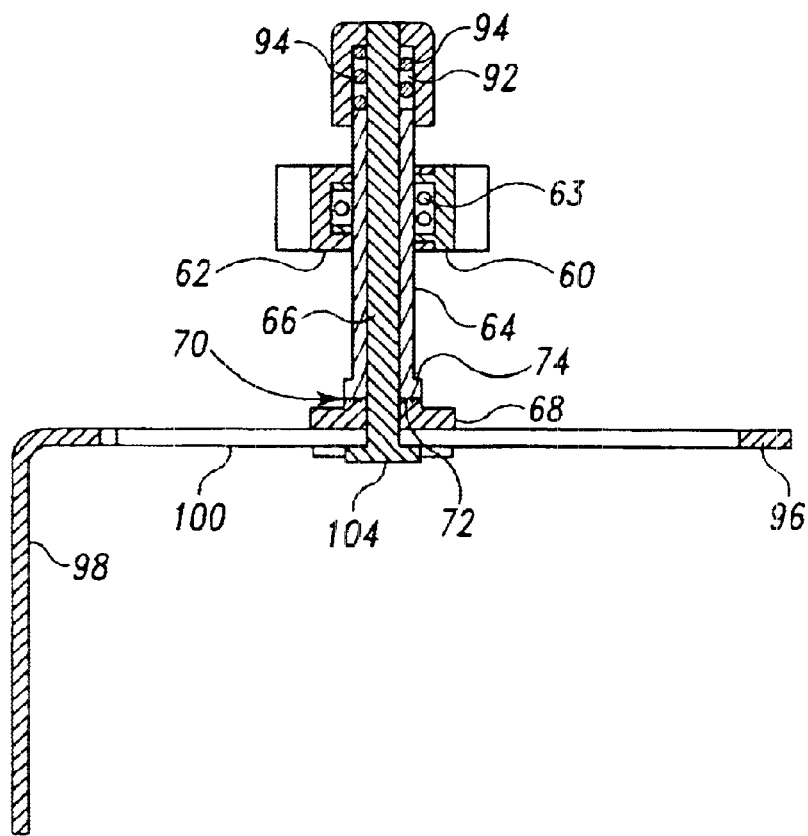
FIG. 8 shows a cross sectional view of the measurement attachment apparatus of FIG. 6 in its normally biased or rest position, taken along line VIII—VIII of FIG. 7.
Figure 9:
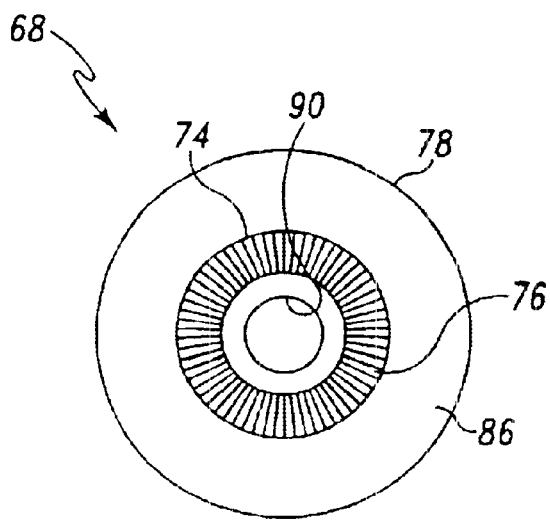
FIG. 9 shows a top plan view of an exemplary embodiment of an arm engagement member for use in the attachment apparatus of FIG. 6.

Referring to FIGS. 6, 7 and 8, the pin attachment apparatus 22 includes the spring-biased clamp 24, a measurement arm 26 and a second spring-biased clamp which in the embodiment described herein is an axial clamp 28. The spring-biased clamp 24 is configured to affix to an anchor point, and more particularly, the pin sleeve 20. The measurement arm 26 is, as discussed above, slidably supported on the spring-biased clamp 24. More specifically, the measurement arm 26 slides with respect to the spring-biased clamp horizontally, which in position over the body, is in the superior-inferior direction along the axis of the femur. (See FIG. 2). The axial clamp 28 is configured to support the measurement arm 26 on the spring-biased clamp. The axial clamp 28 is spring-biased, having a normally-biased locked position and a compressed or actuated position. Preferably, the axial clamp 28 allows both rotational and linear movement of the measurement arm 26 in the compressed position and inhibits rotational and linear movement of the measurement arm 26 in the locked position.

In greater detail, the exemplary spring-biased clamp 24 described herein includes first and second arms 60 and 62, respectively, that terminate in first and second opposing jaws 50 and 52, respectively. Each of the first and second arms 60 and 62 terminates at its other end in one of a pair of handles 58. The first jaw 50 includes a first convex clamping surface 54 and the second jaw 52 includes a second clamping surface 56. The first arm 60 and the second arm 62 pivot about an vertical (anterior-posterior) axis such that opposing pivoting motion of the arms 60, 62 cause the jaws 50, 52 to either move toward each other or move away from each other. A torsion spring 63 is disposed between the arms 60, 62 in such a manner as to urge or bias the jaws 50, 52 toward each other.

The first and second clamping surfaces 54, 56 are preferably configured to cooperate with the pin sleeve 20 to allow for positioning of the spring-biased clamp 24 (and thus the entire pin attachment device 22) at any rotational position about the axis defined by the anchor pin 18 (and pin sleeve 20). Thus, the pin attachment device 22 is effectively rotatable as a unit with respect to the anchor point. The axis of rotation of the pin attachment device 22 is defined by the longitudinal axis of the pin sleeve 20 and anchor pin 18, which is generally vertical (or medial-lateral as shown in FIGS. 1, 2).

The exemplary measurement arm 26 described herein includes an elongate portion 96 that extends relatively horizontally (in the inferior-superior direction). The elongate portion 96 preferably includes measurement indicia 103 which may suitably be in the form of ruled lines. The measurement arm 26 further includes a locator portion 98 that extends angularly from the elongate portion 96. In the exemplary embodiment described herein, the locator portion 98 extends in a normal direction with respect to the elongate portion 96. The locator portion 98 terminates in a pointer end 102. The pointer end 102 is typically defined by one or more tapered edges on the locator portion 96. The elongate portion 96 further includes a central slide channel 100, the purpose of which will become readily apparent further below.

The axial clamp 28 secures the measurement arm 26 to the spring-loaded clamp 24 and facilitates relative linear and rotational motion therebetween. To this end, the exemplary axial clamp described herein includes a stationary shaft 64, a movable shaft 66, and an arm engagement member 68. The stationary shaft 64 extends vertically (in the anterior-posterior direction) and has a hollow interior or bore in which the movable shaft 66 is disposed. The stationary shaft 64 and the movable shaft 66 both have a longitudinal axis that may suitably be the same as the axis of rotation of the first and second arms 60 and 62 of the spring-biased clamp 24. A proximal end of the movable shaft 66 extends out of the stationary shaft 64 and is secured to a cap 92. A distal end of the movable shaft 66 extends out of the other side of the stationary shaft 64, extends through the arm engagement member 68 and terminates in a retention flange 104.

The axial clamp 28 includes a compression spring 94 that biases the movable shaft 66 vertically upward (or laterally in FIGS. 1, 2). To this end, the compression spring 94 is in the exemplary embodiment described herein disposed about the movable shaft 66 between the cap 92 and the proximal end of the stationary shaft 64. The cap 92 extends radially outward from the movable shaft 66 and then axially downward to enclose the compression spring 94. The compression spring 94 normally urges the cap 92 away from the proximal end of the stationary shaft 64, thereby urging the movable shaft 66 upward.

In general, the arm engagement member 68 is located proximate the distal ends of the movable shaft 66 and the stationary shaft 64. The arm engagement member 68 receives the measurement arm 26 in such a manner as to allow sliding or linear movement of the measurement arm 26. The arm engagement member 68 is furthermore rotatable with respect to the spring biased clamp 24, and more particularly, rotatable about the axis defined by the movable shaft 66.

The axis about which the arm engagement member 68 is rotatable is spaced apart from the axis defined by the anchor pin 18. As a result, the measurement arm 26 may be directed in any direction with respect to, and at a selectable distance from, the anchor point. As a result, regardless of the location of the anchor point, the measurement arm 26 may be aligned along the long axis of the femur.

In particular, the axial clamp 28 and the spring-biased clamp 24 each may be rotated about separate axes, thereby creating an adjustable linkage arrangement. As discussed above, the entire pin attachment device 22 is effectively rotatable about the anchor sleeve 20, while the measurement arm 26 is rotatable about the axis defined by the axial clamp 28. The resulting linkage that is formed allows for alignment of measurement arm 26 with respect to the bones of the leg even if the anchor point is not perfectly aligned with such bones.

Figure 12:
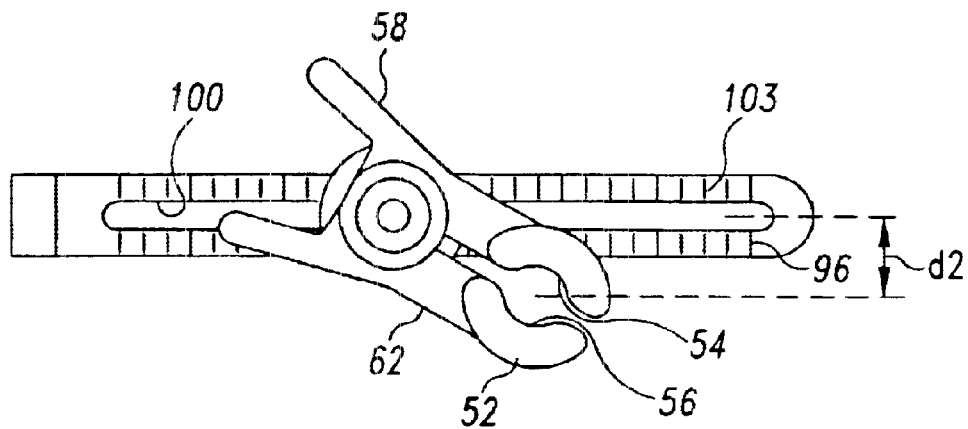
FIG. 12 shows a top plan view of the measurement attachment apparatus of FIG. 6 in a second rotational position.

For example, note in FIG. 7 the distance d1 between the two axes of rotation. The distance d1 represents the offset between the anchor pin 18 and longitudinal axis of the femur, which is represented by the elongate portion 96. FIG. 12, by contrast, illustrates a configuration of the pin attachment device 22 in which the distance between the axes, d2, is much smaller than d1, which accommodates a smaller offset between the anchor pin 18 and the femur.

In the preferred embodiment described herein, the linear movement of the measurement arm 26 and the rotational movement of the arm engagement member 68 are inhibited when the axial clamp 28 is in the normally biased position, as shown in FIG. 8. However, when the cap 92 of the axial clamp 28 is actuated or compressed (see FIG. 13), then the arm engagement member 68 may rotate and the measurement arm 26 may move linearly. Inhibition of movement in the normally biased position "locks" or maintains a particular position of the measurement arm 26 to allow for recording and retaining a particular bone measurement.

More specifically, to selectively inhibit rotational movement, the arm engagement member 68 includes a retention surface 72 that engages an end support surface 74 of the stationary shaft 64. The end support surface 74 defines the distal end of the stationary shaft 64. In order to register and help maintain a select rotational position of the arm engagement member 68, the end support surface 74 and the retention surface 72 include interlocking teeth 70. The interlocking teeth 70 mesh as the axial clamp 28 is released into its normally-biased position. When meshed, the rotational position of the arm engagement member 68 with respect to the spring-biased clamp 24 is maintained.

With reference to FIGS. 6, 8, 9, 10 and 11, an exemplary embodiment of the arm engagement member 68 includes a generally disk-shaped body 78 having a first side 86 and a second side 88. The disk-shaped body 78 defines a central aperture 90. As shown in FIG. 8, the first side 86 includes the end support surface 74 and a set of member teeth 76. The member teeth 76 are the interlocking teeth 70 of the arm engagement member 68. The member teeth 76 extend three hundred, sixty degrees around the end support surface 74 in order to allow rotational registration of the arm engagement member in any position. It is noted that in this embodiment, the end support surface 74 also includes one or more complementary interlocking teeth 70.

In any event, it will be appreciated that the member teeth 76 may be disposed over less than three hundred sixty degrees if suitable rotational stops are employed, or if the end support surface 74 has multiple complementary teeth. In any event, three hundred sixty degrees of rotational freedom allows for more flexible placement of the anchor pin 18.

Figure 11:
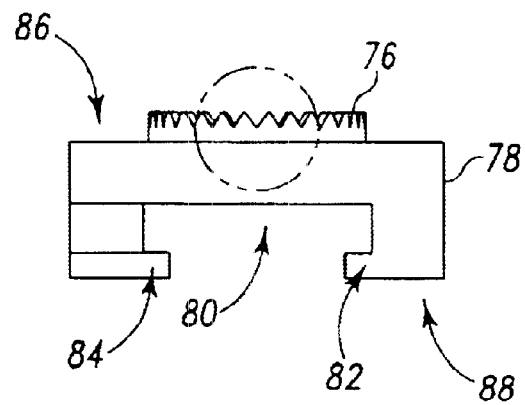
FIG. 11 shows a side plan view of the arm engagement member of FIG. 9.
Figure 10:
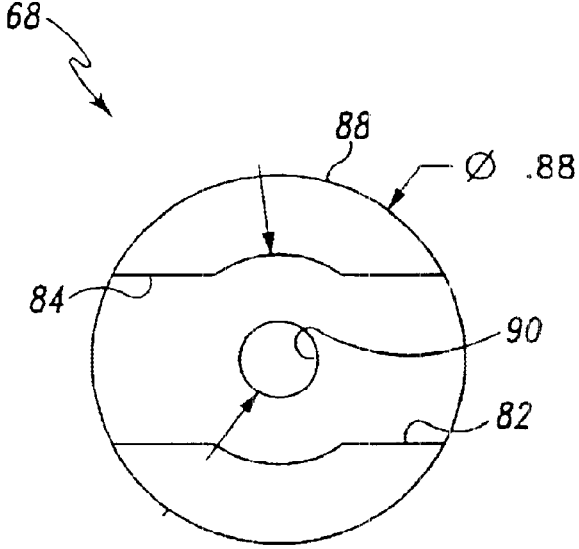
FIG. 10 shows a bottom plan view of the arm engagement member of FIG. 9.

As shown in FIGS. 10 and 11, the second side 88 includes an arm receiving channel 80 defined in the body 78. The arm receiving channel 80 extends throughout the diameter of the body 78 and has a width that corresponds to the width of the elongate portion 96 of the measurement arm 26.

The second side 88 further includes a first overhang 82 and a second overhang 84 that extend over the channel 80. In particular, the overhangs 82 and 84 define a flange or ledge that extends over either side of the channel 80. The overhangs 82 and 84 furthermore preferably extend throughout the length of the channel 80. The overhangs 82 and 84 are configured to provide a positive interference that retains the measurement arm 26 axially within the channel 80.

Referring again generally to FIGS. 8, 9 and 10, the movable shaft 66 extends through the aperture 90 of the arm engagement member 68. The movable shaft 66 further includes, at its distal end, a retention flange 104 that extends radially outward from the movable shaft 66. As assembled, the movable shaft 66 extends passed the end support surface 74 and the retention surface 72, and through the aperture 90 and the slide channel 100 of the measurement arm 26. As a result, the retention flange 104 is positioned axially downward or outward of the measurement arm 26. The radial extension of the retention flange 104 operates to trap the measurement arm 26 and the arm engagement member 68 axially on the movable shaft 66.

It is noted that the slide channel 100 extends most of the length of the elongate portion 96 of the measurement arm 26, but is preferably closed off at either end. Closing off the slide channel 100 advantageously prevents the measurement arm 26 from disconnecting from the pin attachment device 22.

As shown in FIG. 8, the movable shaft 66 is in its naturally biased position, in which the compression spring 94 forces the cap 92 upward, and thus also forces the movable shaft 66 axially upward. The axially upward force urges the retention surface 72 into engagement with the end support surface 74. In particular, the movable shaft 66 is forced upward such that the retention flange 104 forces the measurement arm 26 and the arm engagement member 68 upward until the retention surface 72 engages the end support surface 74. In such a position, the upward bias of the retention flange 104 results in a frictional clamping action that inhibits linear movement of the measurement arm 26 with respect to the arm engagement member 68. In addition, the upward bias of the retention flange 104 also results in the meshing of the interlock teeth 70. The meshing of the interlock teeth 70 inhibits rotational movement of the measurement arm 26.

Figure 13:
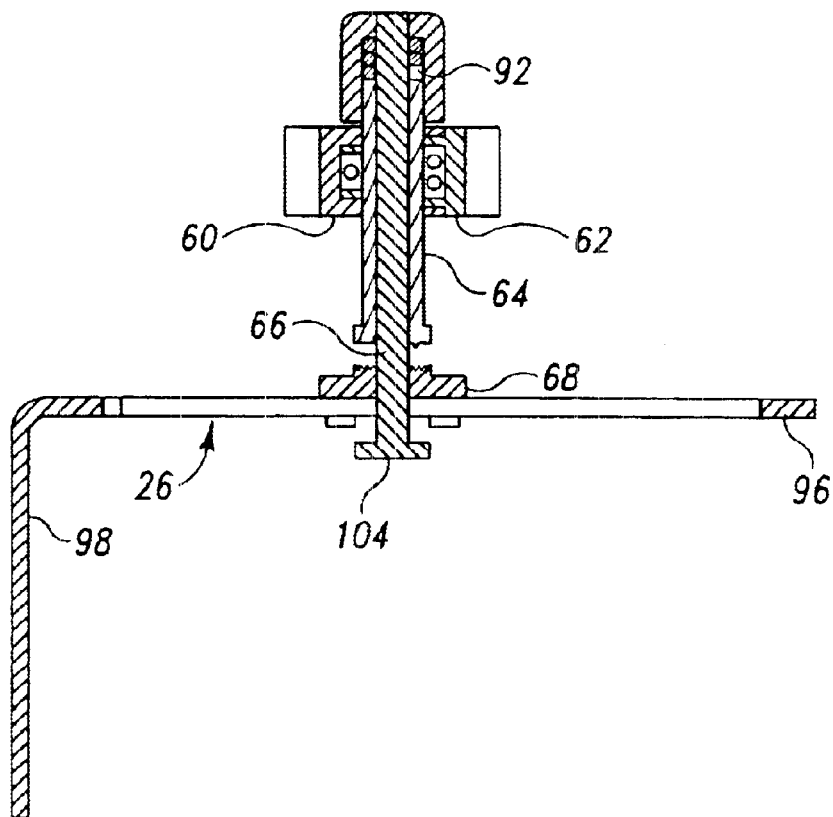
FIG. 13 shows a cross sectional view of the measurement attachment apparatus of FIG. 6 in its actuated or compressed position.

FIG. 13 shows the cross sectional view of the pin attachment device 22 wherein the movable shaft 66 is biased downward away from its naturally-biased position, such that the compression spring 94 is compressed. In this position, the retention flange no longer clamps the measurement arm 26 in place, and the arm engagement member 68 may move axially away from the end support surface 74 of the stationary shaft 64 to permit rotation of the arm engagement member 68. Thus, when the movable shaft 66 is biased downward such as by actuating the cap 92 downward, then the rotational and linear position of the measurement arm 26 may be adjusted. Once the adjustment is over, then the cap 92 is released and the axial clamp 28 resumes its naturally biased position as shown in FIG. 8, wherein rotational and linear movement of the measurement arm 26 is inhibited.

An exemplary surgical method according to the present invention is described below, primarily in connection with FIGS. 1 and 2. In general, the exemplary surgical technique comprises a hip replacement using a posterior approach. While the general bone structure is shown in FIGS. 1 and 2, the muscle and bone structure described in the surgical technique is not shown, but would be known to those of ordinary skill in the art.

First, exposure to the posterior aspect of the hip is provided. The posterior edge of the gluteus medius is identified, and then elevated with a retractor, not shown. The short external rotator and capsule are detached from the posterior border of the greater trochanter 14 and the capsule is split in a T fashion and left attached to the periphery of the acetabulum.

The upper limb or anterior portion of the capsule is retracted superiorly. The anchoring pin 18 is then placed within the pin cavity 44 of the pin sleeve 20. The anchoring pin 18 is thereafter impacted through the capsule and into the ilium 10, preferably in the superior acetabulum. In order to avoid entry into the acetabulum, the anchoring pin 18 is implanted in a vertical alignment.

The surgical leg (including the femur 12) is then placed directly over the underlying leg so that the knees and the ankles are aligned. A cautery knife or surgical pen, not shown, may be used to make a transverse mark on the most lateral portion of the greater trochanter 14.

The pin attachment device 22 is then clipped onto the pin sleeve 20. The cap 92 is actuated to compress the compression spring 94 of the axial clamp 28. While the axial clamp 28 is compressed, the measurement arm 26 is rotated and moved linearly until the pointer end 102 is directly on or adjacent to the scoring mark on the greater trochanter 14 and the elongate portion 96 is aligned with the long axis of the femur 12. Thus, rotation of the measuring arm 26 maybe coupled with possible rotation of the jaws 50 and 52 about the pin sleeve 20 to align the elongate portion 96 with the axis of the femur 12. In such alignment, linear movement of the measuring arm 26 may be used to align the pointer 102 with the mark on the greater trochanter 14. After completing the alignment, the cap 92 is released, thereby locking the linear and rotational position of the measurement arm 26.

The vertical position of the jaws 50, 52 on the pin sleeve 20 is noted. To this end, the location of the jaws 50, 52 is identified using the measurement indicia 42 on the pin sleeve 20. That position represents the offset or lateral offset measurement. In addition, the linear position of the measurement arm 26 is noted using the location of an edge or other feature of the arm engagement member 68 and the measurement indicia 103 on the elongate portion 96. That position represents the length measurement. The pin attachment device 22 and the pin sleeve 20 may then be removed from the anchor pin 18. The axial clamp 28 is preferably left in its naturally biased or "locked" position to retain the rotational and linear position of the measurement arm 26.

Thereafter, the femoral head of the joint 13 is removed. The acetabulum and femur are prepared and trial prosthetic hip devices, not shown, are inserted. Suitable prosthetic hip devices are known. For example, prosthetic hip devices may include an acetabular cup and corresponding ball joint that is attached to an intramedullary bone anchor. In any event, once the trial system is in place, the leg is then repositioned over the opposite leg, matching knees and ankles. The pin sleeve 20 is then replaced onto the anchor pin 18. The pin attachment device 22 is replaced onto the pin sleeve 20.

The surgeon may then repeat the measurement steps described further above and compare the resulting offset measurement and length measurements to the original measurements to ensure that both measurements are substantially similar to the original measurements. If the length measurement is not sufficiently similar, then adjustments may be made to adjust the length. In particular, a different trial device having a different length aspect may be used. In some prosthetics, the length of the prosthetic itself may be adjusted. Similarly, if the offset measurement is not sufficiently similar, then another trial prosthesis may be used, or the existing trial prosthesis may be adjusted.

After adjusting the prosthetic trial components, repeat measurements are taken to determine if the trial provides the appropriate offset and length measurements. As discussed above, appropriate measurements are those that are sufficiently similar to the original measurements, made before removal of the original joint 13. Once appropriate measurements have been achieved, final components having dimensions dictated by the successful trial are implanted. Once the final length and offset measurements are assured, the anchor pin 18 is removed from the ilium 10. Thereafter, closure of the capsule, short rotators, and wound is performed.

One of several advantages of the present invention relates to the ability to accommodate different locations of the anchoring pin 18. In particular, the adjustable linkage provided by the rotation of the clamping surfaces 54, 56 of the spring biased clamp 24 and the rotation of the arm engagement member 68 allows for variable distances between the anchor pin 18 and the long axis of the femur 12. In particular, compare FIG. 7 with FIG. 12. In FIG. 7, the pin attachment device 22 accommodates a relatively large distance d1 between the anchor pin 18 (represented by the central axis between the clamping surfaces 54, 56) and the long axis of the femur (represented by the central line through the elongate portion 96 of the measurement arm 26). By contrast, in FIG. 12, the pin attachment device 22 is adjusted to accommodate a much smaller distance d2 between the anchor pin 18 and the long axis of the femur.

The linkage allows the elongate portion 96 of the measurement arm 26 to nearly always be aligned with the femur 12. Such alignment ensures proper positioning of the leg when attempting to recreate the original measurement condition after the trial prosthesis is implanted.

It will be appreciated that the above described embodiments are merely exemplary, and that those of ordinary skill in the art may readily devise their own implementations that incorporate the principles of the present invention and fall within the spirit and scope thereof.

We claim:

1. An apparatus for use in an arrangement for measuring the relative position of two bones during surgery, comprising:

a spring biased clamp having first and second opposing clamping surfaces, the first and second opposing clamping surfaces adapted to engage and secure the clamp to an anchor in a fixed vertical position, the anchor secured to a first bone location;

a measurement arm comprising an elongate portion and a locator portion extending angularly from the elongate portion, the measurement arm slidably supported on the spring biased clamp, wherein a vertical shaft is interposed between the measurement arm and the spring biased clamp.

2. The apparatus of claim 1 wherein the measurement arm is slidably affixed to a clamping element, the clamping element supported on the vertical shaft.

3. The apparatus of claim 1 wherein the measurement arm is slidably affixed to a clamping element, the clamping element supported on the spring biased clamp.

4. The apparatus of claim 1 wherein the measurement arm is further rotatably supported on the spring biased clamp.

5. The apparatus of claim 1 wherein the first and second opposing clamping surfaces further comprise opposing jaws.

6. The apparatus of claim 1 wherein the spring biased clamp includes opposing clamp handles.

7. The apparatus of claim 1 wherein the first and second opposing clamping surfaces are adapted to engage and secure the clamp to the anchor through a pin sleeve, the pin sleeve including a cavity for receiving a proximal end of the anchor.

8. The apparatus of claim 7 wherein the pin sleeve further comprises measurement indicia.

9. An apparatus for use in an arrangement for measuring the relative positioning of two bones during surgery, comprising:
   a clamp adapted to engage and secure to an anchor in a fixed vertical position, the anchor secured to a first bone location;
   a measurement arm comprising an elongate portion and a locator portion extending angularly from the elongate portion, the measurement arm slidably supported on the clamp, the measurement arm further rotatably supported on the clamp via a spring biased clamping element,
   wherein the spring biased clamping element comprises a stationary shaft, a movable shaft, and an arm engagement member, the stationary shaft including an end support surface, the movable shaft including a retention surface and having a rest position and an actuated position, the movable shaft urging the retention surface toward the end support surface in the rest position, the arm engagement member configured to be secured in a fixed rotational position when said movable shaft is in the rest position.

10. The apparatus of claim 9 wherein the arm engagement member and the end support surface include interlocking teeth, said interlocking teeth inhibiting rotation of the arm engagement member when the movable shaft is in the rest position.

11. The apparatus of claim 9 wherein the movable shaft further includes a retention flange, the retention flange urging the measurement arm against the arm engagement member to inhibit linear movement of the measurement arm with respect to the arm engagement member when the movable shaft is in the rest position.

12. An apparatus for use in an arrangement for measuring the relative positioning of two bones during surgery, comprising:
   a clamp adapted to engage and secure to an anchor in a fixed vertical position, the anchor secured to a first bone location;
   a measurement arm comprising an elongate portion and a locator portion extending angularly from the elongate portion, the measurement arm slidably supported on the clamp, the measurement arm further rotatably supported on the clamp via a spring biased clamping element; and
   a vertical shaft disposed between the clamp and the measurement arm.

13. The apparatus of claim 12 wherein the clamp further comprises a spring loaded clamp.

14. The apparatus of claim 12 wherein the clamp further comprises first and second opposing jaws.

15. The apparatus of claim 12 wherein the first and second opposing clamping surfaces are adapted to engage and secure the clamp to the anchor through a pin sleeve, the pin sleeve including a cavity for receiving a proximal end of the anchor.

16. The apparatus of claim 15 wherein the pin sleeve further comprises measurement indicia.

17. An apparatus for use in an arrangement for measuring the relative distance between two bones during surgery, comprising:
   a clamp adapted to engage and secure to an anchor in a fixed vertical position, the anchor secured to a first bone location; and
   a measurement arm comprising an elongate portion and a locator portion extending angularly from the elongate portion, the measurement arm slidably supported on the clamp, the measurement arm further rotatably supported on the clamp at a position in which an axis of rotation of the measurement arm is spaced apart from a longitudinal axis of the anchor,
   wherein the clamp is adapted to be rotatable about the longitudinal axis of the anchor.

18. The apparatus of claim 17 wherein the clamp further comprises first and second opposing jaws.

19. The apparatus of claim 17 wherein the clamp further comprises a spring loaded clamp.

20. The apparatus of claim 19 wherein the measurement arm is further rotatably supported on the clamp via a spring biased clamping element.

21. The apparatus of claim 17 wherein the measurement arm is further rotatably supported on the clamp via a spring biased clamping element.

22. An apparatus for use in an arrangement for measuring the relative distance between two bones during surgery, comprising:
   an anchor configured to be affixed to a first bone;
   a clamp adapted to engage and secure to the anchor in a fixed vertical position, the anchor secured to a first bone location; and
   a measurement arm comprising an elongate portion and a locator portion extending angularly from the elongate portion, the measurement arm slidably supported on the clamp, the measurement arm further rotatably supported on the clamp at a position in which an axis of rotation of the measurement arm is spaced apart from a longitudinal axis of the anchor,
   wherein the clamp is adapted to be rotatable about the longitudinal axis of the anchor.

23. The apparatus of claim 22 wherein the anchor comprises a pin.

24. The apparatus of claim 23 wherein the anchor further comprises a pin sleeve.

25. The apparatus of claim 22 wherein the clamp further comprises first and second opposing jaws.

26. The apparatus of claim 22 wherein the clamp further comprises a spring loaded clamp.

27. The apparatus of claim 26 wherein the measurement arm is further rotatably supported on the clamp via a spring biased clamping element.

28. The apparatus of claim 22 wherein the measurement arm is further rotatably supported on the clamp via a spring biased clamping element.

* * * * *